United States Patent
Gray et al.

(10) Patent No.: US 9,103,842 B2
(45) Date of Patent: *Aug. 11, 2015

(54) METHODS FOR REJUVENATING RED BLOOD CELLS

(71) Applicant: Biomet Biologics, LLC, Warsaw, IN (US)

(72) Inventors: Alan Gray, North Reading, IN (US); Joel C. Higgins, Claypool, IN (US); Matthew D. Landrigan, Fort Wayne, IN (US); Grant Cunningham, Warsaw, IN (US)

(73) Assignee: Biomet Biologics, LLC, Warsaw, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/844,773

(22) Filed: Mar. 15, 2013

(65) Prior Publication Data

US 2014/0212397 A1 Jul. 31, 2014

Related U.S. Application Data

(63) Continuation-in-part of application No. 13/756,116, filed on Jan. 31, 2013.

(51) Int. Cl.

| | |
|---|---|
| *A61K 35/18* | (2015.01) |
| *C12N 5/078* | (2010.01) |
| *G01N 33/80* | (2006.01) |
| *A61K 31/19* | (2006.01) |
| *A61K 31/70* | (2006.01) |
| *A61K 31/7076* | (2006.01) |
| *A61K 35/14* | (2015.01) |

(52) U.S. Cl.
CPC ............... *G01N 33/80* (2013.01); *A61K 31/19* (2013.01); *A61K 31/70* (2013.01); *A61K 31/7076* (2013.01); *A61K 35/14* (2013.01)

(58) Field of Classification Search
None
See application file for complete search history.

(56) References Cited

U.S. PATENT DOCUMENTS

| | | |
|---|---|---|
| 4,116,646 A | 9/1978 | Edwards |
| 5,250,303 A | 10/1993 | Meryman et al. |
| 7,723,017 B2 | 5/2010 | Bitensky et al. |
| 2005/0074743 A1 | 4/2005 | Purmal et al. |
| 2005/0233302 A1 | 10/2005 | Hess et al. |
| 2011/0256522 A1 | 10/2011 | Ericson et al. |
| 2012/0077182 A1 | 3/2012 | Bitensky et al. |
| 2013/0004937 A1 | 1/2013 | Yoshida et al. |
| 2014/0065117 A1 | 3/2014 | Gray |

FOREIGN PATENT DOCUMENTS

| | | |
|---|---|---|
| EP | 0987034 A2 | 3/2000 |
| WO | 0113933 A2 | 3/2001 |
| WO | 2011103179 A1 | 8/2011 |
| WO | 2014039660 A1 | 3/2014 |

OTHER PUBLICATIONS

Lockwood et al., Transfusion, 2003, vol. 43, p. 1527-1532.*
Klein et al., The Lancet, 2007, vol. 370, p. 415-426.*
Liu et al., Anal. Chem., 2005, vol. 77, p. 573-578.*
COBE 2991 Cell processor, 2008, 4 pages of PDF.*
Resnick et al., A J Med Sci, 1994, Feb. 307, Suppl. 1, S66-9, Abstract Only.*
Stan et al., Rom. J. Intern. Med., 2009, vol. 47, No. 2, p. 173-177.*
Brecher, M.E. et al. Rejuvenation of erythrocytes preserved with AS-1 and AS-3. A.J. Clin. Path. 96(6):767-769. 1991.
Burger, Patrick et al. An improved red blood cell additive solution maintains 2, 3-diphosphoglycerate and adenosine triphosphate levels by an enhancing effect on phosphofructokinase activity during cold storage. Transfusion, vol. 50, No. 11, (Nov. 29, 2010), pp. 2386-2392.
Button, L. et al. "Rejuvenation of red blood cells drawn in ADSOL to extend autologous red cell storage" (Abstract S54) Transfusion 26(6): 558, 1986.
D'Alessandro, Angelo et al. Red blood cell strage: the story so far. Blood Transfus, (Mar. 29, 2010), pp. 82-88.
Dufour SP, et al; Erythrocyte-Dependent Regulation of Human Skeletal Muscle Blood Flow: Role of Varied Oxyhemoglobin and exercise on nitrite, S-nitrosohemoglobin, and ATP. Am J Physiol Heart Circ Physiol 299:H1936-H1946, (2010).
Haemonetics, ACP 215 Automated Cell Processor (2012).
Heaton, A. et al. "Use of ADSOL preservation solution for prolonged storage of low viscosity AS-1 red blood cells." Br. J. Haemo. 57:467-468, 1984.
Hess, J.R. An update on solutions for red cell storage. Vox Sanguinis, vol. 91, No. 1 (Jul. 1, 2006) pp. 13-19.
Hess, John R., Red cell storage. Journal of Proteomics, Elsevier, Amsterdam, NL., vol. 73, No. 3, (Jan. 3, 2010), pp. 368-373.
Rathbun, E.J. "Posttransfusion survival of red cells frozen for 8 weeks after 42-day liquid storage in AS-3." Transfusion 29(3):213-217, 1989.
Rejuvenation Handbook, A Comprehensive Guide to Red Cell Rejuvenation, enCyte™ Systems Inc., Brochure, (1977).
reJuvesol® Red Blood Cell Processing Solution, enCyte™ Systems, Inc., Brochure (Mar. 1997).
Reynolds JD, et al. "The Transfusion Problem: Role of Aberrant S-Nitrosylation" Transfusion, 51:852-858, 2011.
Roback, John D., Vascular Effects of the Red Blood Cell Storage Lesion, Ameriacan Society of Hematology, Transfusion Medicine, Adverse Complications of Stored Blood, Hematology (2011).
Song et al. "Multiplexed volumetric bar-chart chip for point-of-care diagnostics" Nat Commun. (2012) 3:1283.
Spiess et al. Pro: Autologous blood should be available for elective cardiac surgery. Journal of Cardio Thoracic and Vascular Anesthesia, Saunders, Philadelphia, PA, US, vol. 8, No. 2 (Apr. 1, 1994), pp. 231-237.

(Continued)

*Primary Examiner* — Kade Ariani
(74) *Attorney, Agent, or Firm* — Harness, Dickey

(57) ABSTRACT

Methods for transfusing blood to a mammalian subject. The method includes obtaining a unit of blood, rejuvenating the blood with an enhancement composition, measuring 2,3-DPG concentration of the blood, and delivering the blood to a subject.

20 Claims, 4 Drawing Sheets

(56) References Cited

OTHER PUBLICATIONS

Valeri, C.R. "Simplification of the method for adding and removing glycerol during freezing preservation of human red blood cells with the high or low glycerol methods: Biochemical Modification prior to freezing." Trasfusion 15(3):195-218, 1975.

Valeri, C.R. et al. The survival, function and hemolysis of human RBCs stored at 4C in additive solution (AS-1, AS-3 or AS-5) for 42 days and then biochemically modified, frozen, thawed washed and stored at 4C in sodium chloride and glucose solution for 24 hours. Transfusion, American Association of Blood Banks, Bethesda, MD, US, vol. 40 (Nov. 1, 2000), pp. 1341-1345.

Valeri, C.R. et al. "A clinical experience with ADSOL preserved erythrocytes" Surg. Gyn. Obs. 166:33-46, 1988.

Valeri, C.R. et al., "Automation of the glycerolization of red blood cells with the high-separation bowl in the Haemonetics ACP 215 Instrument" Transfusion 2005, vol. 45, p. 1621-1627.

Valeri, C.R., Rejuvenation and Freezing of Outdated Stored Human Red Cells, New England Journal of Medicine 287:1.307-1313 (Dec. 28, 1972).

Van De Watering, L.M. G, et al. Beneficial Effects of Leukocyte Depletion of Transfused Blood on Postoperative Complications in Patients Undergoing Cardiac Surgery: A Randomized Clinical Trial. Circulation, vol. 97, No. 6, (Feb. 17, 1998), pp. 562-568.

Veale, Margaret F. et al. Effect of additive solutions on red blood cell (RBC) membrane properties of stored RBCs prepared from whole blood held for 24 hours at room temperature. Transfusion Jan. 2011, vol. 51, Suppl 1, (Jan. 2011), pp. 255-335.

Yoshida, T., et al. The effects of additive solution pH and metabolic rejuvenation on anaerobic storage of red cells, Transfusion, vol. 48, No. 10, (Oct. 1, 2008), pp. 2096-2105.

Zimrin, A.B. et al. Current issues relating to the transfusion of stored red blood cells. Vox Sanguines, vol. 96, No. 2, (Feb. 1, 2009), pp. 93-103.

Caridian BCT. COBE Spectra, Apheresis System. "Customized White Blood Cell Collections" 2009.

Hospira. "GemStar Pump Set-SL, Nonvented with 0.2 Micron Filter, 96 Inch." (2012).

Lockwood et al. "Effects of Rejuvenation and Frozen Storage on 42-Day-Old AS-3 RBCs" Transfusion, (Nov. 2003) vol. 43, pp. 1527-1532.

Meyer, E K. et al. "Rejuvenation capacity of red blood cells in additive solutions over long-term storage." Transfusion. Jul. 2011, vol. 51, No. 7: 1574-1579.

Resnick, LM et al., "Is the Higher Incidence of Ischemic Disease in Patients with Hypertension and Diabetes Related to Intracellular Depletion of High Energy Metabolites?" Am J Med Sci Feb. 1994; 307 Suppl 1:S66-9.

Scott, K. L. et al. "Biopreservation of Red Blood Cells: Past, Present, and Future" Transfusion Medicine Reviews, Grune and Stratton, Orlando, FL (2005) vol. 19 No. 2: 127-142.

\* cited by examiner

METHODS FOR REJUVENATING RED BLOOD CELLS

CROSS-REFERENCE TO RELATED APPLICATIONS

This application is a continuation-in-part of U.S. patent application Ser. No. 13/756,116 filed on Jan. 31, 2013. The entire disclosure of the above application is incorporated herein by reference.

INTRODUCTION

The present disclosure relates to methods for transfusing blood to mammalian subjects, and a system for use with the methods.

Transfusion of blood is an important aspect of treating many disorders and injuries, such as treatment of accident victims and during surgical procedures. According to current American Red Cross statistics, about 5 million people receive blood transfusions yearly in the United States alone. A single accident victim can require as many as 100 pints of blood. Thus, the collection and distribution of blood and blood products is a vital part of the health care system. Typically, blood is obtained from a donor and then processed and stored; units of stored blood or blood products are then taken from storage as needed and transfused into a patient in need. In some cases, the blood may be an autologous donation, where an individual donates blood in expectation of receiving his or her own blood by transfusion during or after a medical procedure.

Donated blood is typically processed into components and then placed in storage until needed. Short term storage can be as long as six weeks, although blood or blood components can be frozen and stored for as long as ten years. Unfortunately, the storage of red blood cells (RBCs) is associated with "storage lesions," altering their energy production, oxygen delivery capacity, redox status, and structural/membrane integrity. For example, the concentration of adenine triphosphate (ATP) in stored RBCs decreases over time. Not only is ATP an energy source used by cells to catalyze numerous enzymatic reactions, ATP also signals endothelial cells to release nitric oxide (NO), which is a potent vasodilator. Additionally, the concentration of 2,3-diphosphoglycerate (2,3-DPG) within RBCs is significantly reduced after 14 days of storage, and is often undetectable after 21 days of storage. 2,3-DPG enhances the ability of RBCs to release oxygen by interacting with deoxygenated hemoglobin, decreasing the hemoglobin's affinity for oxygen, and thereby promoting the release of the remaining oxygen bound to the hemoglobin. Therefore, with diminished levels of ATP and 2,3-DPG, an RBC's ability to oxygenate tissue is severely impaired.

To rejuvenate RBCs before administration into a patient, blood can be incubated with an enhancement composition containing materials that increase intracellular concentrations of 2,3-DPG and ATP, improving the ability of RBCs to oxygenate tissues. Such enhancement compositions typically comprise one or more active materials such as inosine, adenine, sodium pyruvate and sodium phosphate (dibasic and monobasic). A useful enhancement composition is Rejuvesol® Red Blood Cell Processing Solution (Rejuvesol® Solution), which has been marketed by Cytosol Laboratories Inc. (now Citra Labs, LLC) since 1991.

While such compositions are effective to improve the metabolic activity of RBCs, there remains a need to develop compositions and methods that improve efficacy. Moreover, it has been discovered that such compositions may have particular utility during medical procedures treating certain disorders.

SUMMARY

The present technology provides methods for transfusing blood to a mammalian subject, including such methods for the treatment of disorders associated with reduced tissue oxygenation. The methods comprise adding a red blood cell metabolic enhancement composition (herein "enhancement composition") to a volume of red blood cells, incubating the treated blood composition, and administering the incubated blood composition to the mammalian subject. In some embodiments, the incubated blood composition is washed prior to administration to the subject. In some embodiments, methods further comprise measuring one or both of 2,3-DPG and ATP concentrations in the blood, prior to administering to the subject.

Aspects of the methods, such as the washing and the steps of adding the enhancement composition to the red blood cells, may be performed at the point of care for the mammalian subject. Such processes may be continuous, using a system proximate to the subject at the point of care, in fluid communication Methods can be performed immediately after blood is collected from a donor and prior to preservation, or the method can be performed after blood is removed from preservation, immediately before administration to a subject. Before the method is performed, the blood can be processed to become red blood cell concentrated (RBCC), or leukocytes can be removed to generate leukoreduced RBCs.

The present technology also provides a method for transfusing RBCs to a subject, at a point of care, comprising obtaining a volume of donated RBCs, adding an enhancement composition to the volume of donated RBCs to form a treated blood composition, incubating the treated blood composition to form an incubated RBC composition, diluting the incubated RBC composition with wash solution to form a diluted RBC composition, centrifuging the diluted RBC composition, forming a concentration of RBC and a supernatant, and administering the incubated blood composition to a subject. After washing, the washed RBC composition can be centrifuged to form a concentration of RBCs and a supernatant. The supernatant can be removed and the concentration can be mixed with in an additive solution, to form a resuspended RBC composition.

In various embodiments, methods comprise obtaining a volume of blood from a human or other mammalian subject, separating blood to isolate red blood cells, rejuvenating the red blood cells with an enhancement composition to form rejuvenated blood, measuring the 2,3-DPG concentration in in the rejuvenated blood, calculating the volume of rejuvenated blood necessary to dose the subject to normal or higher levels of 2,3-DPG, and delivering the rejuvenated blood to the subject. Such methods may be performed at a point of care. The fraction of blood remaining after separation may be administered to the subject, or may be used to suspend the red blood cells after rejuvenation.

Methods of the present technology include the administration of treated blood to mammalian subjects suffering with an ischemic disorder. For example, blood treated with an enhancement composition may be administered to a subject in anticipation of an ischemic event, such as surgery.

DRAWINGS

Figure 1:
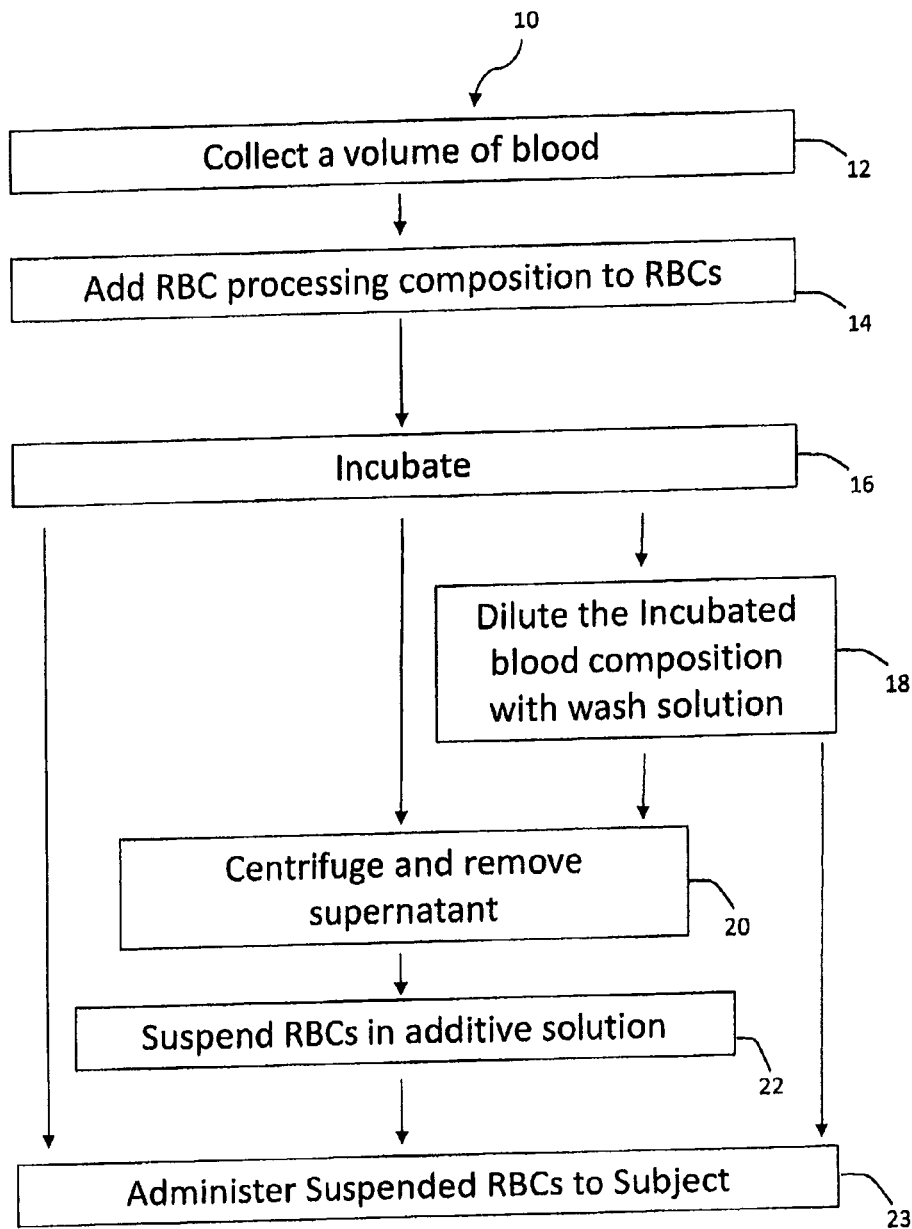
FIG. 1 is a diagrammatic illustration of a representative method for transfusing blood.

It should be noted that the figures set forth herein are intended to exemplify the general characteristics of an apparatus, materials and methods among those of the present technology, for the purpose of the description of certain embodiments. These figures may not precisely reflect the characteristics of any given embodiment, and are not necessarily intended to define or limit specific embodiments within the scope of this technology.

DETAILED DESCRIPTION

The following description of technology is merely exemplary in nature of the subject matter, manufacture and use of one or more inventions, and is not intended to limit the scope, application, or uses of any specific invention claimed in this application or in such other applications as may be filed claiming priority to this application, or patents issuing therefrom. A non-limiting discussion of terms and phrases intended to aid understanding of the present technology is provided at the end of this specification.

The present technology relates to methods of processing whole blood or a blood fraction comprising red blood cells (herein, unless specifically stated otherwise, referred to as "blood") using a composition (referred to herein as an "enhancement composition") which improves one or more metabolic functions of blood. Such compositions may comprise a rejuvenating material selected from the group consisting of inosine, adenine, pyruvate, phosphates, and mixtures thereof. The present technology includes diagnostic tests for determining 2,3-DPG and/or ATP concentrations in blood.

RBC Metabolic Enhancement Compositions

The present technology provides enhancement compositions which restore, increase or otherwise enhance, directly or indirectly, one or more metabolic functions of red blood cells. As further discussed below, in some embodiments, enhancement compositions increase the production or concentration of one or more intracellular constituents associated with the biochemical or biomechanical function of red blood cells, including oxygen transport, oxygen release or other metabolic parameters which affect the ability of blood to oxygenate tissue. As discussed further below, in some embodiments enhancement compositions increase the intracellular concentrations of one or both of adenine triphosphate (ATP) and 2,3-diphosphoglycerate (2,3-DPG).

In some embodiments, enhancement compositions of the present technology can comprise safe and effective amounts of inosine, pyruvate, adenine and phosphate. A "safe and effective" amount of a rejuvenating material is an amount that is sufficient to have the desired effect on the biochemical or biomechanical function of RBCs, without undue adverse side effects on the viability of RBCs or other blood components or a subject to whom the RBCs are administered (such as toxicity, irritation, or allergic response), commensurate with a reasonable benefit/risk ratio when used in the manner of this technology. The specific safe and effective amount of the rejuvenating material will, obviously, vary with such factors as the metabolic state of the RBCs, the specific rejuvenating material(s) used, the conditions under which the RBCs are processed with the rejuvenating material, and physical condition of the subject to whom the RBCs are administered.

In various embodiments, the inosine can have a concentration of from about 25 g/L to about 30 g/L. Preferably, the concentration of inosine can be about 25.0 g/L, about 25.5 g/L, about 26.0 g/L, about 26.2 g/L, about 26.4 g/L, about 26.6 g/L, about 26.8 g/L, about 27.0 g/L, about 27.5 g/L, about 28.0 g/L, about 28.5 g/L, about 29.0 g/L, about 29.5 g/L, or about 30.0 g/L. In various embodiments, the pyruvate can have a concentration of from about 5 g/L to about 15 g/L. Preferably, the concentration of pyruvate can be about 5 g/L, about 6 g/L, about 7 g/L, about 8 g/L, about 9 g/L, about 10 g/L, about 11 g/L, about 12 g/L, about 13 g/L, about 14 g/L, or about 15 g/L. In various embodiments, the adenine can have a concentration of from about 0.2 g/L to about 2 g/L. Preferably, the concentration of adenine can be about 0.2 g/L, about 0.3 g/L, about 0.4 g/L, about 0.5 g/L, about 0.6 g/L, about 0.7 g/L, about 0.8 g/L, about 0.9 g/L, about 1.0 g/L, about 1.1 g/L, about 1.2 g/L, about 1.3 g/L, about 1.4 g/L, about 1.5 g/L, about 1.6 g/L, about 1.7 g/L, about 1.8 g/L, about 1.9 g/L, or about 2.0 g/L. The phosphate can be a mixture of a monobasic monohydrate salt and a dibasic heptahydrate salt. The phosphate can be a salt of sodium phosphate. The ratio of monobasic salt to dibasic salt can be from about 1:2 to about 1:3. More specifically, the monobasic salt:dibasic salt ratio can be about 1:2.0, about 1:2.10, about 1:2.15, about 1:2.20, about 1:2.25, about 1:2.30, about 1:2.35, about 1:2.40, about 1:2.45, about 1:2.50, about 1:2.55, about 1:2.60, about 1:2.65, about 1:2.70, about 1:2.75, about 1:2.80, about 1:2.85, about 1:2.90, about 1:2.95, or about 1:3.0. The phosphate mixture can have a final concentration of from about 18 g/L to about 22 g/L. More specifically, the concentration of phosphate mixture can be about 18 g/L, about 18.5 g/L, about 19 g/L, about 19.5 g/L, about 20 g/L, about 20.1 g/L, about 20.2 g/L, about 20.3 g/L, about 20.4 g/L, about 20.5 g/L, about 20.6 g/L, about 20.7 g/L, about 20.8 g/L, about 20.9 g/L, about 21 g/L, about 21.5 g/L, or about 22 g/L.

In some embodiments, enhancement composition comprise:

(i) from about 25 g/L to about 30 g/L of inosine;
(ii) from about 0.2 g/L to about 2 g/L of adenine;
(iii) from about 5 g/L to about 15 g/L of pyruvate; and
(iv) from about 17 g/L to about 23 g/L of sodium phosphate.

For example, an enhancement compositions may comprise:

(a) about 27 (e.g, 26.8) g/L inosine;
(b) about 11 g/L pyruvate (e.g., sodium pyruvate);
(c) about 0.7 (e.g., 0.681) g/L adenine; and
(d) about 21 (e.g., 20.8) 1 g/L phosphate (e.g., a mixture of about 6.21 g/L monobasic, monohydrate; and about 14.6 g/L dibasic, heptahydrate).

Preferably, the composition has a pH of from about 6.5 to about 7.5, more preferably from about 6.6 to about 7.4, more preferably from about 6.7 to about 7.1, more preferably from about 6.7 to about 7.0. An enhancement composition useful in the methods of this technology has been commercialized by Citra Labs, LLC (formerly Cytosol Laboratories), Braintree, Mass., under the mark "Rejuvesol®".

Methods of Processing Blood

The present technology also provides methods of processing whole blood or a blood fraction comprising red blood cells (herein, unless specifically stated otherwise, referred to as "blood") using an enhancement composition of this technology, as described above. Such methods comprise, for example:

1) mixing blood with an enhancement composition; and
2) incubating the mixture of blood and enhancement composition.

The blood treated in the present methods may be obtained from a mammalian subject (a "donor") using methods among those well known in the art. In various embodiments the donor is a human subject. The blood may be allogeneic (i.e., donated by a subject of the same species) or autologous (obtained by the subject to whom the treated blood is to be administered, such as may be drawn in advance of a surgical procedure).

Processing of blood using an enhancement composition of the present technology may be performed on blood that has been stored or may be performed on "fresh" blood at a time proximate to the time it is withdrawn from the donor. (As used herein, a "proximate" time is any time 24 hours or less after an initial event (e.g., donation of blood), such as concurrent with the event, or 24 hours, 18 hours, 12 hours, 6 hours, 4 hours, 2 hours, 1 hour, 30 minutes, 15 minutes, 10 minutes, 2 minutes, 1 minute, or less, after the initial event.) The volume of blood can be concentrated, by removal of at least a portion of blood plasma, to produce red blood cell concentrate (RBCC). Storage may be, for example, from 1 to 50 days, or longer, as needed. Storage may be at any temperature and other conditions to as to maintain viability of the RBCs for clinically acceptable storage period. For example, storage may be at a temperature of from about 1° C. to about 6° C. In other embodiments, the RBCs may be frozen, at a temperature of about −65° C. or lower, with the addition of conditioning agents that preserve the viability of the RBCs at such low temperatures. Suitable conditioning agents (cryopreservatives) include glycerol. It is understood that such conditioning agents are to be removed from the RBCs prior to administration, such as by methods described below for removal of cryopreservatives prior to administration.

In some embodiments, the volume of blood is leukoreduced prior to use in the processes of the present technology. Such leukoreduced blood contains fewer leukocytes than whole blood, and may, in some embodiments, be essentially free of leukocytes. Other blood components may also be removed from leukoreduced blood, either before, during, or after removal of the leukocytes.

Incubating the mixture is conducted for a time sufficient to allow RBCs in the blood to assimilate components from the enhancement composition and achieve a desired effect on a biochemical or biomechanical function of RBCs. Without limiting the scope of methods, composition and uses of the present technology, the incubation may increase the metabolic activity of RBCs (for example, in the glycolysis, pentose phosphate, and amino acid pathways), restoring a metabolic profile in the RBC close to those in fresh RBC. This restored profile may result in improved RBC function in the transfusion recipient including oxygenation of tissues, nitric oxide (NO) production capacity, and reduced risk of adverse effect from the transfusion. For example, incubation may be conducted for a time sufficient to increase the concentration of ATP and 2,3-DPG in RBCs. The time may vary, depending on such factors as the desired level of increase of ATP and 2,3-DPG, the use of mechanical agitation, the amount of enhancement composition used, and temperature of the blood during incubation. In some embodiments, about 50 ml of enhancement composition is added to RBCs derived from up to about 550 ml of whole blood. Mixing can be performed by swirling, shaking, rotating, or agitating.

In some embodiments, the blood is tested during incubation to determine whether one or more desired biochemical or biomechanical attributes of the RBCs have been attained. Thus, for example, incubation may be conducted until a desired level of ATP, 2,3-DPG, NO or other biochemical marker of RBC function is attained, e.g., essentially equal to levels found in fresh blood.

Methods for measuring such markers of RBC function useful herein include methods among those known in the art. For example, 2,3-DPG can be detected by assay kits that are commercially available. In one such assay, 2,3-DPG from blood is split by phosphoglycerate mutase (PGM), when PGM is activated by glycolate-2-phosphate, to produce phosphoglycerate (PG) and inorganic phosphate ($P_i$). Both 2-PG and 3-PG can be formed, but 2-PG is isomerized by PGM to form 3-PG. In the presence of ATP, 3-PG is converted to 1,3-DPG by phosphoglycerate kinase (PGK). Next, 1,3-DPG is converted to glyceraldehyde-3-P by glyceraldehyde-3-phosphate dehydrogenase (GAP-DH) and the oxidation of NADH. Glyceraldehyde-3-P is converted to digydroxyacetone-P by triosephosphate isomerase (TIM), and dihydroxyacetone-P is converted to glycerol-3-P by glycerol-3-phosphate dehydrogenase (GDH) and the oxidation of NADH. The oxidation of the two NADH molecules can be monitored spectrophotometrically at a wavelength of 340 nm. Where necessary, standard curves can be prepared with standard solutions of 2,3-DPG. A kit useful in such methods is commercially available from Roche Diagnostics Corporation—Roche Applied Science (Indianapolis, Ind.), for the determination of 2,3-DPG in blood in the range of 0.02-0.15 μmol. In some embodiments, a sample of blood can be taken directly from a subject, or from a closed system used in a continuous process (as described below), for the 2,3-DPG determination. The difference between the 2,3-DPG before and after blood has been rejuvenated can be determined.

In another method, as an alternative to measuring 2,3-DPG, the partial pressure of $O_2$ gas required to achieve 50% hemoglobin saturation ($P_{50}$) is measured. For example, the $P_{50}$ can be measured at a point of care by use of a GEM Premier 3000 (Instrumentation Laboratory Company, Bedford, Mass.). In particular, a blood sample is mixed with heparin to prevent coagulation. Then, a drop or two of the blood sample is expelled onto a gauze pad. The gauze pad is then positioned at the GEM Premier 3000 for the $P_{50}$ analysis. This analysis can be performed before and after the blood has been rejuvenated.

2,3-DPG can also be detected by ELISA-based techniques. In one embodiment, 2,3-DPG in a blood sample can be quantitated by a 2,3-DPG ELISA Kit commercialized by Novus Biologicals (Littleton, Colo.). Wells of an assay plate are coated with anti-2,3-DPG antibodies. Adding blocking buffer comprising non-fat dry milk or bovine serum albumin to the wells will block sites in the wells that are not coated with the antibody. The wells are then washed one or more times with a washing buffer, such as phosphate buffered saline (PBS). A sample of plasma is injected into at least one well, and various amounts of standard 2,3-DPG is added to wells to form a standard curve. Additionally, 2,3-DPG coupled to biotin (2,3-DPG-biotin) is added to every well. The 2,3 DPG in the sample and in the wells comprising a the standard curve competes with the 2,3-DPG-biotin for binding to the anti-2,3-DPG antibodies. The assay plates are then incubated for about 30 minutes to about 60 minutes at about 37° C. The wells are then washed another 3 to 5 times. Next, avidin conjugated to horseradish peroxidase (avidin-HRP) is added to each well. The avidin binds the biotin coupled to 2,3-DPG. After washing another 3-5 times, an HRP substrate, such as 3,3',5,5'-tetramethylbenzidine (TMP) is added. HRP catalyzes the reduction of $H_2O_2$ with TMP used as a proton donor. The reaction produces TMP diimine, which is blue. Absorbance of the blue TMP diimine can be measured on a spectrophotometer with a microplate reader at a wavelength of 450 nm. The amount of 2,3-DPG in a blood sample can be determined by comparing the absorbance of the plasma sample with the standard curve.

In another embodiment, multiple small strips can be used in place of an assay plate. A strip would comprise an end composed of a material that is transparent to visible light, such as polystyrene or methacrylate. The end would comprise a small well. The small well can be coated with anti-2,3-DPG antibodies. Unlike the method described above, a user could dip the end of the strip into a blood or plasma sample processed to contain biotin-2,3-DPG. Strips could also be dipped into solutions of various standard concentrations of 2,3-DPG. After incubating, the strips can be washed. The ends of the strips can then be dipped into a solution comprising avidin-HRP, or the avidin-HRP could be pipetted into the wells. Unbound avidin-HRP is then washed out of the wells. The end of the strips are then either dipped into a TMP substrate solution comprising TMP, water, and $H_2O_2$, or the substrate solution can be pipetted into the wells. The strips can then be inserted into a reader that geometrically accepts the strips so an absorbance reading can be made at the well at a wavelength of 450 nm.

Another embodiment is based off of an ELISA assay performed on a Vchip as described by Song, et al., Nat Commun. 2012; 3:1283. Doi: 10.1038/ncomms2292. Vchips are microfluidic chips comprising a plurality of wells and channels, and two plates. The V chips have a top end and a bottom end. When one plate slides relative to the second plate, flow channels are formed. Therefore, a variety of components can be preloaded into a Vchip via flow lanes before a reaction occurs. A top flow lane is preloaded with ink or dye. The flow lane second from the top is precoated with anti-2,3-DPG antibodies and then loaded with a plasma sample processed to contain biotin-2,3-DPG. After an incubation period, this lane can be washed to prevent non-specific signals. Flow lanes below the second flow lane from the top are separately filled with avidin-conjugated catalase (avidin-catalase) and the catalase substrate, peroxide ($H_2O_2$). In the presence of catalase, $H_2O_2$ is broken into $H_2O$ and $O_2(g)$. Separate flow channels are formed when one plate is slid relative to the other. Formation of the flow channels causes the components of the flow lanes to mix. The avidin-catalase binds to biotin-2,3-DPG and the catalase reaction ensues. The $O_2(g)$ released by the reaction causes the ink/dye in the top lanes to flow upwards through the flow channels. The more $O_2(g)$ produced, which is dependent upon the amount of 2,3-DPG binding to the antibodies, the further the ink/dye will travel.

ATP can be detected in blood by a bioluminescence assay. One such assay utilizes luciferase (typically recombinant firefly luciferase), which in the presence of ATP, converts luciferin to oxyluciferin. The oxyluciferin is produced in an electronically excited state. Therefore, the oxyluciferin releases a photon of light as it returns to its ground state. To measure the ATP present in blood, a blood sample can be drawn from a patient or from tubing containing treated or untreated blood. A small sample of the blood can be mixed with a luciferin/luciferase solution. The solution can be a buffer, such as a Tricine buffer, pH 7-8, containing luciferin, luciferase, and $Mg^{2+}$. The ATP in the blood sample will activate the reaction, which results in luminescence. The luminescence can be detected in a luminometer. Measurements can be taken before and after blood has been rejuvenated. Although the reagents for this ATP assay are individually available through multiple vendors, some vendors offer kits that comprise all the reagents. One such kit is the ATP Determination Kit (A22066) from Molecular Probes, Inc. (Eugene, Oreg.; now Life Technologies, Carlsbad, Calif.).

In another embodiment, Luciferase can be immobilized onto a solid support by: (a) physical adsorption; (b) entrapment; or (c) covalent attachment/crosslinking (Spahn et al., Recent Patents on Engineering 2008, Vol. 2, No. 3). The solid support can be a test strip with a small sample chamber. The enzyme could be immobilized within the sample chamber. Blood would be processed by adding a volume of luciferin to it. The blood:luciferin mix can be pipetted into the sample chamber, or the mix can be loaded by capillary action. In the presence of ATP from the blood, the immobilized luciferase will convert the added luciferin to oxyluciferin in a reaction that produces luminescence. The strip can be placed in a handheld or desktop luminomitor for analysis.

In another method, an end of a test strip can comprise a small sample well and microelectrodes. The microelectrodes can be coated with glycerol kinase and glycerol-3-phosphate oxidase. Blood would be processed by adding a volume of glycerol to it. Glycerol kinase converts ATP and glycerol to glycerol-3-phosphate (plus ADP), and glycerol-3-phosphate oxidase converts the glycerol-3-phosphate to glycerone phosphate+$H_2O_2$. Therefore, when the test strip is placed into an analyzer that comprises a terminal that contacts the microelectrodes, the $H_2O_2$ can be detected by amperometry.

In various embodiments, 2,3-DPG or ATP concentrations are performed by 2,3-DPG testing device and an ATP testing device (collectively "testing devices"). The testing devices can be robustly and physically attached to a unit (or one device to several units) of blood, a standalone unit, or part of a total rejuvenation device. Therefore, in one embodiment, it is envisioned that a device (a tag, a chip, a glass plate, a pregnancy test-style strip, etc.) can be sterilely affixed to a unit of blood. Alternatively, sterile samples can be obtained for single or repeat testing from red blood cell or a blood filled integral tubing segment, comprising multiple vents, which is part of the original blood bag or are sterilely attached using a sterile connection device (SCD). Upon a need to test a unit of blood, the sterile link between the unit of blood and the testing device can be open allowing for testing to take place. The vents enable smooth flow of blood. Multiple vents provide a means for multiple segments of tubing to be removed. Either device could be attached to such a unit of blood or or numerous devices attached in order to allow for repeated testing.

In another embodiment, a bag of blood can be non-sterilely penetrated to obtain a sample for 2,3-DPG or ATP testing, which necessitates prompt usage if the unit of blood is sufficient levels of 2,3-DPG or ATP to be used. Such penetration could be performed by use of a Y-set or by drawing a sample of blood through a port for testing in a device separate from the unit of blood.

Additionally, fresh blood can be obtained from a patient to measure 2,3-DPG in order to determine whether in-situ rejuvenation is required. This test may also be performed subsequent to in-situ rejuvenation of a patient or after rejuvenation of a unit of blood using Rejuvesol® Solution.

By the preceding measures, a point of care diagnostic method measures the level of 2,3-DPG for determining whether to immediately deliver a unit of blood, rejuvenate and then deliver a unit of blood, test a current unit of blood to determine additional storage time, determine the volume of blood need to return a patient to normal, or higher than normal blood levels of 2,3-DPG and/or ATP, or in any instance, perform a diagnostic test on the blood prior to and subsequent to any rejuvenation. Normal blood levels may be from about 12.7 to about 1.7 μmoles/l/Hb The blood may be incubated with an enhancement composition for a predetermined time, such as from about 30 seconds to about 24 hours. If the blood is to be stored prior to administration, incubation may occur throughout the period in which blood is stored, as discussed further below. For example, the blood can be incubated with an enhancement composition for from about 5 minutes to about 90 minutes, or from 15 minutes to about 60 minutes, at a temperature of from about 1° C. to about 45° C., or from about 25° C. to about 40° C., such as at about 37° C. In some embodiments, the blood is incubated for about 30 minutes.

Incubation can be performed using a variety of devices and methods among those known in the art. For example, blood can be incubated by immersing a bag containing the mixture of blood and enhancement composition in a recirculating water bath. In another embodiment, incubating can be performed for about 5 minutes to about 60 minutes (such as for about 30 minutes) in a thawing device with a bath temperature set at from about 25° C. to about 45° C. Thawing devices include ThermoLine Models: MT202, MT204, or MT210 sold by Helmer Scientific, Noblevilles, Ind., USA, (formerly ThermoGenesis, Corp, Rancho Cordova, Calif., USA). In another example, incubating can be performed by placing the treated blood composition in an insulated box containing about 6 instant hot gel packs, wherein the temperature within the insulated box is from about 25° C. to about 45° C. A device can be placed within the insulated box to mix the treated blood composition, or the insulated box can be rotated in such a way that the treated blood composition is mixed from within. A plasma thawer such as the Sahara 3, commercially available from Sarstedt AG & Co., can be used to agitate, warm and incubate the units.

The treated blood may be stored after incubation, or may be administered to a mammalian subject in need of blood. Conditions for storage include those discussed above. In some embodiments, the administration is at a time proximate to the time when the blood is obtained and treated using methods of the present technology.

In some embodiments, the processed RBC compositions of the present technology are sterilized. Sterilization can be performed by any pharmaceutically acceptable method, including such methods as are known to those of ordinary skill in the art. Non-limiting examples of sterilization include heating, autoclaving, irradiation, and filtering.

Methods may further comprise washing the blood after incubation to remove all, or a portion, of the components and by-products of the enhancement composition. Washing can be performed using methods among those known in the art, including such methods as are used for processing frozen blood to remove glycerol prior to transfusion. For example, washing may comprise adding a wash solution to a liquid volume of RBCs, centrifuging the resulting mixture to form a concentration (e.g, a pellet) of RBCs, and removing the supernatant. Wash solutions may include, for example, normal saline. Such washing may be performed with devices known in the art, such as the ACP® 215 Automated Cell Processor, sold by Haemonetics Corporation, Braintree, Mass. The washing may be performed at a time proximate to administration of the blood to a mammalian subject.

In some embodiments, methods comprise removing liquid components of the incubated red blood cell composition prior to administration to a mammalian subject. Such methods further comprise, for example, centrifuging the incubated red blood cell composition, forming a concentration of red blood cells, and a supernatant; and isolating the concentration of red blood cells. The concentration of red blood cells may then be suspended in an mixing solution, forming a red blood cell suspension that may be administered to a mammalian subject. Additive solutions include those known in the art suitable for storage or administration of blood, including normal saline. In some embodiments, such methods further comprising adding a wash solution, such as normal saline, to the incubated red blood cell composition prior to the centrifuging. Thus, methods of the present technology include those comprising:

(a) obtaining a volume of red blood cells from a mammalian subject;
(b) adding an enhancement composition to the volume of red blood cells, forming a treated blood composition;
(c) incubating the treated blood composition, forming an incubated red blood cell composition;
(d) centrifuging the incubated red blood cell composition, forming a concentrate of red blood cells, and a supernatant;
(e) isolating the concentrate of red blood cells; and
(f) mixing of the concentrate of red blood cells in additive solution, forming a red blood cell suspension.

Optionally, the process may further comprise diluting the incubated red blood cell composition with wash solution prior to the centrifuging step.

Methods of the present technology may be continuous, wherein two or more sequential steps (e.g., adding an enhancement solution and incubating) are performed on a flow of RBCs, substantially without interruption through the process steps. Thus, for example, a liquid volume of RBCs may flow through an apparatus which adds enhancement solution, subjects the mixture of RBCs and enhancement solution to isolation conditions (e.g., heating and mixing). Such a flow may then continue in a continuous manner to further process steps, including addition of a washing solution, centrifugation, and suspension of RBCs. As discussed below, such processes may be performed in an automated closed system in fluid communication with an intravenous catheter.

Methods of Transfusing and Treatment

The present technology relates to methods for transfusing blood to a subject. Such methods comprise any procedure suitable for administering to a mammalian subject a liquid volume of blood comprising RBCs that have been processed according to a method of this technology. As further discussed below, transfusing may be performed pursuant to any medically appropriate procedure, such as for the treatment of diseases or disorders associated with blood loss or reduced blood function. Alternatively, transfusing may be performed in anticipation of surgery in order to medical optimize the subject to withstand the rigors associated with surgical stress. Specific methods for administration include those known in the art, such as through use of an intravenous catheter. Specific methods for administration include those known in the art, such as through use of an intravenous catheter.

The present technology provides methods where the processing of blood is performed at a time proximate to the administration of the processed blood. For example, as defined above, such proximate administration of blood may be performed 24 hours, 18 hours, 12 hours, 10 hours, 8 hours, 4 hours, 1 hour, 30 minutes, 15 minutes, 10 minutes, 2 minutes, 1 minute, or less, after incubation of the red blood cells. In some processes, the methods are "point of care," wherein the processes of the present technology are performed at a location proximate, such as in the same room (for example, bed side) or otherwise immediately adjacent, to the mammalian subject to be transfused with the RBCs. As further discussed below, such point-of-care processes may be performed using a system comprising an apparatus adapted to perform two or more sequential steps of a process of the present invention, such as the steps of obtaining blood, adding an enhancement composition, incubating, washing, and administering. In some embodiments, such a system is in fluid communication with a device, such as an intravenous catheter, for obtaining blood from a subject or administering blood to a subject. In some embodiments, the RBCs administered are autologous.

As discussed above, a subject in need of a transfusion can have a disorder characterized by reduced tissue oxygenation. Such disorders include those wherein when blood flow is fixed, restricted, reduced, or stopped. Furthermore, blood transfusions can be necessary when blood is lost though injury, surgery or disease. Subjects and disorders that may be treated include: subjects with sepsis or septic shock that are anemic and require a blood transfusion; subjects with Upper Gastrointestinal Bleeding ("UGIB") that are anemic and require a blood transfusion; subjects subjected to severe trauma that are anemic and require a blood transfusion; subjects that are critically ill (adult and pediatric) in an intensive care unit, who are anemic and require a blood transfusion; subjects that under-go open heart surgery and receive a blood cardioplegia solution to perfuse the heart during hypothermic, ischemic cross-clamp, thus providing better oxygenation of the myocardium during open-heart surgery; subjects suffering a stroke, treating ischemic brain tissue following a stroke, thus increasing the oxygen delivery capacity of the systemic circulation via exchange transfusion or by direct administration to the ischemic area via arterial catheter or by retrograde perfusion via the venous circulation; subjects undergoing obstetrical complications, subjects with bleeding ulcers; subjects with hemolytic anemia; subjects with thrombocytopenia, pneumonia and acute respiratory distress.

Further to the discussion above of methods involving centrifugation of incubated RBC volume, FIG. 1 shows an exemplary method 10 for transfusing blood to a mammalian subject. In step 12, a volume of blood is collected from a donor. The volume of blood can be obtained from the subject to whom the blood will be transfused, i.e. autologous blood, or the volume of blood can be allogeneic from a suitable donor. In some embodiments, the volume of blood is stored in various additive solutions, commonly used in the art, at 1° C.-6° C. In some embodiments, the volume of blood is cryopreserved. The volume of blood can be processed by concentrating to produce red blood cell concentrate (RBCC), or by removing leukocytes to produce leukoreduced RBCs (LR-RBCs; whereas non-leukoreduced blood is NLR-RBC). In yet other embodiments, the volume of blood is treated with a red blood cell (RBC) enhancement composition before being stored. Alternatively, the method 10 can be performed at a time proximate to when the volume of blood is collected.

In step 14, an enhancement composition is added to the volume of RBCs, forming a treated blood composition. The enhancement composition can be transferred through a functionally-closed sterile fluid pathway, such as described below. Next, in step 16, the treated blood composition is incubated, forming an incubated blood composition.

In optional step 18, the incubated blood composition can be diluted with saline or other wash solution, to form a diluted blood composition. The incubated blood composition can be transfused within 24 hours of washing.

In step 20, the incubated blood composition from step 16, or the diluted blood composition from step 18, is centrifuged. Centrifuging results in a concentrate of RBCs and a supernatant. The supernatant can be removed. In optional step 22, the concentrate of RBCs is mixed with an additive solution, such as saline.

Finally, in step 23, any of the incubated blood composition from step 16, the diluted blood composition form step 18, or the resuspended blood composition from step 22 can be transfused to a subject.

Figure 2:
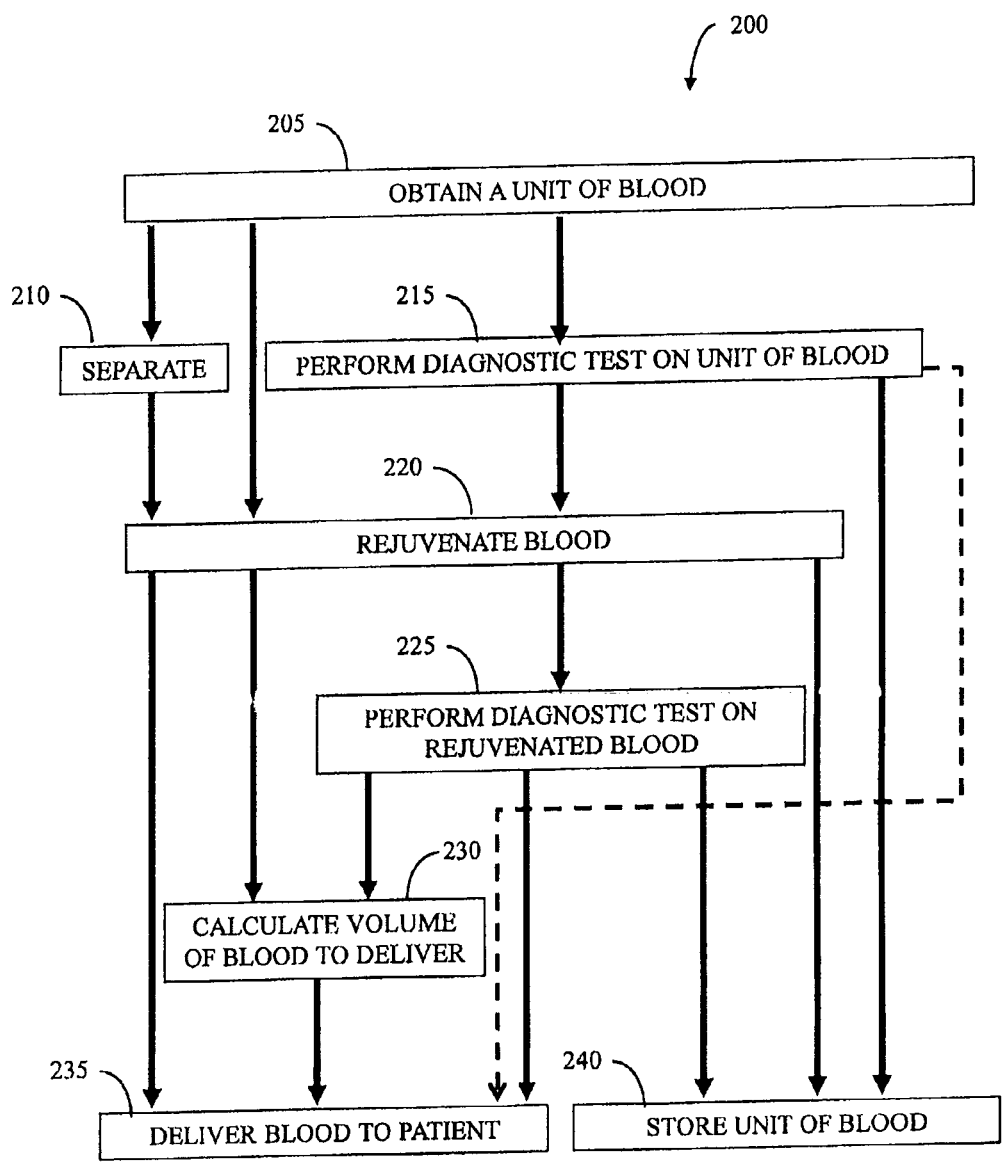
FIG. 2 is a diagrammatic illustration of a representative method for performing diagnostics on, and rejuvenating, blood.

With reference to FIG. 2, a method 200 for preforming diagnostics for 2,3-DPG and/or ATP, and rejuvenating red blood cells at a point of care can include the diagrammatically illustrated aspects. In step 205, a unit of blood is obtained. The unit of blood can be from a subject in need of treatment (autologous), or it can be from a subject different from the subject in need of treatment (allogeneic). Furthermore, whether autologous or allogeneic, the blood can be drawn at a point of care, i.e. in an operating room or in a medical facility, or the blood can be obtained from storage, i.e. a blood bank. When blood is obtained at a point of care, it can be drawn through an intravenous (IV) line.

After obtaining blood in step 205, the blood can undergo separations in step 210. Blood can be drawn directly from a patient through an IV line and into an separation device (such as an apheresis device). During separation, blood is drawn into a separation device, fractionated into red blood cell, buffy coat, and plasma fractions, at least one fraction is removed, and at least one fraction is delivered back to the patient. Unlike traditional separation, which comprises removal of a buffy coat and/or plasma and delivery of red blood cells back to the patient, step 210 comprises removal of the red blood cells and delivery of the buffy coat and plasma back to the patient.

The oxygenating capabilities of the collected red blood cells can be enhanced in step 220 by rejuvenation. Treating the red blood cells with Rejuvesol® Red Blood Cell Processing Solution (Rejuvesol® Solution), commercialized by Citra Labs, LLC (Braintree, Mass.), can rejuvenate the red blood cells. Rejuvenated red blood cells have ATP and/or 2,3-DPG concentrations equal to or greater than levels normally found in blood. For example, fresh, normal blood has a concentration of 2,3-DPG of from about 8.86-16.64 µmol/L/gHb. Therefore, a diagnostic test can be performed on the rejuvenated blood in step 225. Diagnostic tests include tests that measure ATP and/or 2,3-DPG concentrations in rejuvenated blood. Measuring ATP and/or 2,3-DPG concentrations can be performed by any method commonly used in the art and by methods described herein. These methods include electrochemical methods, methods comprising the use of antibodies, e.g. ELISA, or chemical methods. Methods described herein are fast, accurate, and particularly useful for the method 200. Rejuvenated blood is characterized by normalized or increased ATP and/or 2,3-DPG concentration values relative to normal blood, and the blood's increased ability to oxygenate tissue. Alternatively, the red blood cells can be delivered to the patient in step 235 immediately after the rejuvenation step 220.

In step 230, the measured 2,3-DPG concentration in rejuvenated blood can be used to determine the total number of units of the rejuvenated blood necessary for dosing a patient to return 2,3-DPG levels to that of normal blood, or higher. Whether step 230 is performed or not, the rejuvenated blood can be delivered to the patient in step 235. When a patient has been dosed with rejuvenated blood with a 2,3-DPG concentration greater than a corresponding concentration in normal blood, the blood's oxygenating capabilities are enhanced. Such an enhancement is beneficial to a patient suffering from ischemia, or for "medically optimizing" a patient who will shortly thereafter undergo surgery.

As mentioned above, step 205 can include obtaining blood from a living donor or from a blood bank. In either scenario, the blood to be delivered in step 235 can be autologous or allogeneic to the patient in need of a transfusion. When apheresis is not necessary, the blood obtained in step 205 can undergo a diagnostic test in step 215, as discussed above, or it can be rejuvenated in step 220. When blood is obtained from a donor within hours of performance of method 200, i.e. fresh, the need for it to be rejuvenated is minimal. Notwithstanding, rejuvenating fresh blood can lead to blood with 2,3-DPG levels of about 150% (about 18 µmol/L/gHb) or higher than that of the fresh blood. Such blood has an exceptionally enhanced ability to oxygenate ischemic tissues. Conversely, old blood, or blood that has been in storage for longer than about 8 days, typically has decreased 2,3-DPG and ATP levels and decreased oxygenating capability. Measuring the ATP and/or 2,3-DPG concentration values in step 215 provides information about the state of the blood obtained in step 205. Low values, i.e. values less that about 8.0 µmol/L/gHb indicate the blood has a low metabolic activity and a weak ability to oxygenate tissue. To obtain an intended beneficial impact of a transfusion with such blood, the old blood should be rejuvenated with Rejuvesol® Solution in step 220. Additionally, blood can be placed into storage in step 240 after either performing a diagnostic test in step 215 or rejuvenating blood in step 220.

After the blood has been rejuvenated in step 220, an additional diagnostic test can be performed in step 225. This test will provide information regarding how much the concentrations of 2,3-DPG and/or ATP increased after the rejuvenation step 220 relative to the respective concentrations measured with the diagnostic test performed in step 215 (if step 215 was indeed previously performed). In optional step 230, the measured 2,3-DPG and/or ATP concentrations in rejuvenated blood can be used to determine the total number of units of the rejuvenated blood necessary for dosing a patient to return 2,3-DPG and/or ATP levels to that of normal blood, or higher. Whether optional step 230 is performed or not, the rejuvenated blood can be delivered to the patient in step 235. If performing a diagnostic test on rejuvenated blood in step 225 was not performed, then calculating the volume of rejuvenated blood necessary to dose a patient to normal or higher levels of 2,3-DPG and/or ATP cannot be performed. In such a scenario, step 230 is skipped and the blood rejuvenated in step 220 can be delivered to a patient in need thereof in step 235. Alternatively, after a diagnostic test is performed on rejuvenated blood in step 225, the rejuvenated blood can be stored in step 340.

Systems

As discussed above, processes of the present technology may be performed in a system apparatus adapted to perform two or more sequential steps of a process of the present invention in a continuous process. For example, one such system comprises:
(a) an incubation system, for mixing an enhancement composition with a volume of RBCs, which may be in fluid communication with a supply volume of the enhancement solution, and which may comprise a temperature control device for maintaining the temperature of the volume of RBCs during incubation;
(b) a washing system, for adding a washing solution to incubated RBCs;
(c) a centrifugation system, for isolating RBCs from the liquid volume of incubated RBCs; and
(d) a suspension system for adding a volume of additive solution to the isolated RBCs, to form an RBC suspension.

In some point of care embodiments, the system is in fluid communication with an intravenous catheter or other device by which the RBC suspension is directly administered to a subject. In the alternative, or in addition, the system may be in communication with a second intravenous catheter for obtaining a volume of whole blood directly from a subject, which may be the same subject to which the RBC suspension is administered.

In some embodiments, the system is automated, such that one or more steps of a process of this technology are performed without substantial intervention by a clinical operator during the process steps. Preferably, such systems are "closed," to minimize or eliminate exposure of the RBCs, the enhancement composition and other compositions used in the process to microbial contamination.

As discussed above, incubation of the blood may be conducted until a desired level of a biochemical marker of RBC function is attained. Thus, the incubation system may comprise a measurement device by which an aliquot of blood may be obtained and tested for the concentration of the marker, and the duration of incubation adjusted accordingly. For example, 2,3-DPG can be detected online by injecting reagents for a 2,3-DPG assay, such as is available from Roche Diagnostics Corporation—Roche Applied Science (Indianapolis, Ind.), as described above, into a tube of the closed system. The tube can comprise a transparent section, such as made from quartz, which can be positioned in a spectrophotometer. The difference between the 2,3-DPG before and after blood has been rejuvenated can be determined. In another embodiment, ATP can be detected online in a closed system, by injecting a luciferin/luciferase solution (as described above) into a transparent section of tubing in the system that contains blood. This transparent section of tubing can be enclosed in a dark box wherein no external light can enter. A photomultiplier tube (PMT) connected to an external computer is positioned immediately below the transparent tubing within the dark box. The PMT can detect light produced by the assay, and a computer can display the results. Measurements can be taken before and after blood has been rejuvenated.

Figure 3:
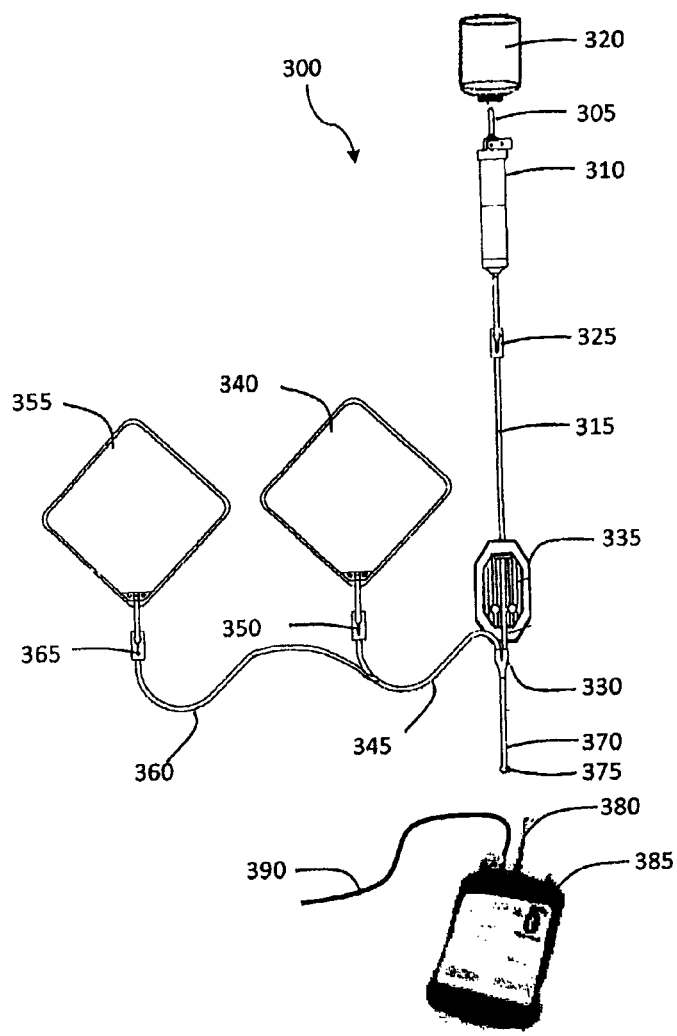
FIG. 3 is a diagrammatic illustration of an apparatus for improving the metabolic function of blood.

FIG. 3 depicts a closed, Y-type tube set 300 system useful in methods of the present technology. The tube set 300 includes a vented spike 305 with drip chamber 310 coupled to the distal end of a first tube 315. Spike 305 can be inserted into a blood treatment vial 320 or bottle to complete a fluid communication channel between the interior of blood treatment vial 320 and first tube 315. The blood treatment vial 320 can include an enhancement composition. Also, a first clip 325 can be coupled to the first tube 315 to regulate flow through first tube 315.

First tube 315 is coupled at its second end to an input of a Y-shaped connector 330. An in-line micro-biotic barrier filter 335 is positioned in the first tube 315 flow path to filter the material flowing from the vented spike 305 through the first tube 315 to the input of Y-shaped connector 330. One exemplary in-line micro-biotic barrier filter 335 is a flat 0.2 micron filter.

A transfer bag 340 can be coupled to a first end of a second tube 345. The second end of second tube 345 is coupled to the other input of Y-shaped connector 330. Transfer bag 340 can be initially empty and used to collect, for example, supernatant waste material. Additionally or alternatively, transfer bag 340 may initially include a processing agent, such as a wash solution. A second clip 350 can be coupled to the second tube 345 to regulate flow through second tube 345. Further, a second transfer bag 355 can be coupled to the second tube 345 by a third tube 360. The second transfer bag 355 can be initially empty and used to collect, for example, supernatant waste material. Additionally, or alternatively, transfer bag 340 may initially include a processing agent, such as an additive solution. A third clip 365 be coupled to the second tube 345 to regulate flow through second tube 345.

Fourth tube 370 can be coupled to the output of the Y-shaped connector 330 at its first end. A second end of fourth tube 370 is defined by a seal 375 sealing the fluid channel of fourth tube 370. For example, seal 375 can be welded closed or to a fifth tube 380 coupled to a blood bag 385 using a radio frequency (RF) tube sealer (not shown). Additionally, the blood bag 385 can comprise a sixth tube 390 that can transfer treated blood to a subject. Given that no potential entry point of the Y-type tube set 300 is initially unsealed or unprotected by a micro-biotic barrier filter, this Y-type tube set 300 is functionally-closed. In other words, the Y-type tube set 300 provides a functionally-closed, sterile fluid pathway (via fourth tube 370) for blood enhancement composition from bottle 380 to be delivered into the blood bag 385.

Because the blood enhancement composition can be transferred to the volume of donated blood by a sterile, functionally-closed fluid pathway, the blood can be stored for more than 24 hours after such delivery. Additional post-processing devices can be used to further process the blood while maintaining the blood in a functionally-closed, sterile environment. For example, the volume of donated blood can be processed using a functionally-closed, sterile centrifuge. This can be done, for example, prior to delivering the enhancement composition to the volume of donated blood, contained in a blood bag, to remove components of whole blood and leave RBCs in the blood bag. One exemplary functionally-closed, sterile centrifuge is the COBE Spectra Apheresis System. Post-wash storage beyond 24 hours can be achieved using "functionally closed" blood cell processing systems such as the Haemonetics Blood Cell Processor model ACP 215.

Methods and systems among those of the present technology are illustrated in the following non-limiting examples.

Example 1

A Y-type tube set is assembled is assembled as shown in FIG. 2 and connected to a unit of RBCs. The tube set includes a 0.2 µm filter. RBC enhancement composition (Rejuvesol® Solution) is transferred to the RBCs via a vented spike to form a treated blood composition. The treated blood composition is mixed and incubated, forming an incubated blood composition. The treated blood composition is centrifuged to form a concentration of RBC and a supernatant. The supernatant is transferred to an empty waste bag, and the concentration of RBCs was resuspended in 100 mL additive solution that was transferred from a second transfer bag.

Example 2

A Y-type tube set is assembled as shown in FIG. 2 and connected to a unit of 250 mL RBCs. 100 mL additive solution, comprising saline, was transferred to the RBCs. The tube set includes a 0.2 µm filter. 50 mL RBC enhancement composition (Rejuvesol® Solution) was transferred to the RBCs via a vented spike to form a treated blood composition. The treated blood composition was mixed and incubated, forming an incubated blood composition. The incubated blood composition was then diluted with 200 mL wash solution from a first transfer bag containing 200 mL wash solution, forming a diluted blood composition. The diluted blood composition was centrifuged to form a concentration of RBCs and a supernatant. The supernatant was transferred to the now empty first transfer bag, and the concentration of RBCs was resuspended in 100 mL additive solution, which was transferred from a second transfer bag.

Figure 4:
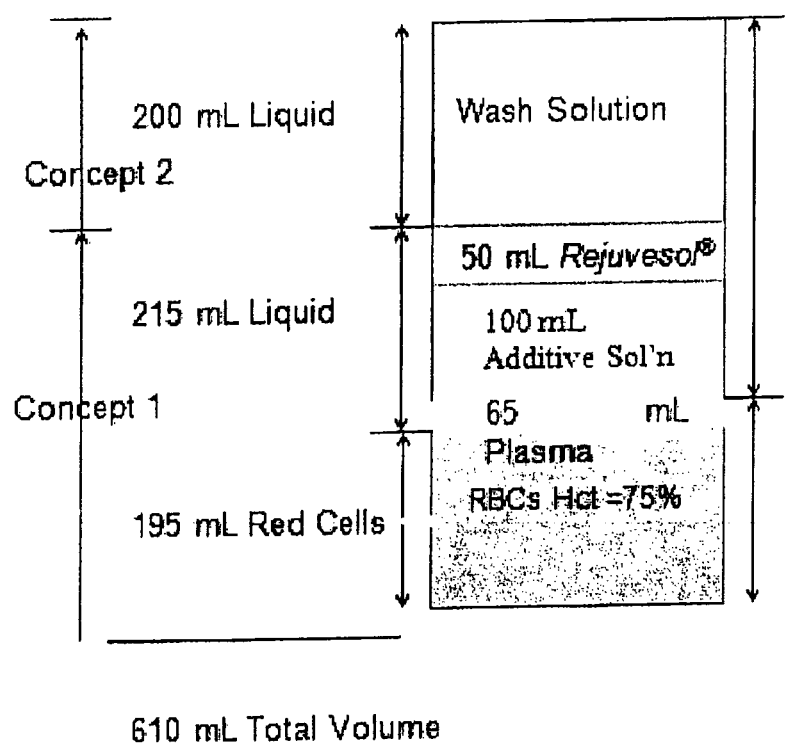
FIG. 4 is a diagrammatic illustration of two concepts for performing a method of the present technology.

The processing of blood as described in Examples 1 and 2 results in differing dilutions of Rejuvesol® constituents, as depicted in FIG. 4 and described below.

Concept 1 Dilution of Rejuvesol® 215 mL=4.3
50 mL

The concentration of each constituent in Rejuvesol® is >100 mMol/L and would be >23.3 mMol/L after centrifugation and removal of 75% of all supernatant where an estimated residual volume of 53.8 mL remains in the red cells.

$$\text{Initial}=23.3\text{mMol/L} \times 0.215\text{mL}=5.01\text{mMol}$$

$$\text{Final}=23.3\text{mMol/L} \times 0.0538\text{L}=1.25\text{mMol}$$

Est. % Residual of each constituent=25%

Concept 2 Dilution of Rejuvesol® 350 mL=7
50 mL

The concentration of each constituent in Rejuvesol® is >100 mMol/L and would be >14.3 mMol/L after dilution, centrifugation, and removal of 75% of all supernatant where an estimated residual volume of 53.8 mL remains in the red cells.

$$\text{Initial}=14.3\text{mMol/L} \times 0.350\text{mL}=5.01\text{mMol}$$

$$\text{Final}=14.3\text{mMol/L} \times 0.0538\text{L}=0.769\text{mMol}$$

Est. % Residual of each constituent=15%

Blood processed according to Examples 1 and 2 are analyzed for concentrations of rejuvenation materials in the final processed RBC suspensions, with the following results.

TABLE 1

| | | Plasma Concentration in vivo* after transfusion of one unit of 2,3-DPG Enhanced Cells | | |
|---|---|---|---|---|
| Constituent or Metabolite | Reference Concentration in Serum or Plasma (mMol/L) | Without Further Processing (mMol/L)** | Concept 1, assumes 75% Removal (mMol/L) | Concept 2, assume 85% Removal (mMol/L) |
| Pyruvate | 0.034-0.102 | 2.19 | 0.55 | 0.33 |
| Adenine | n/a | 0.110 | 0.027 | 0.016 |
| Inosine | n/a | 2.19 | 0.55 | 0.33 |
| Phosphates | 0.74-1.52 | 2.19 | 0.55 | 0.33 |
| Lactate | 0.3-2.2 | 2.19 | 0.55 | 0.33 |
| Uric Acid | 0.16-0.51 | 2.19 | 0.55 | 0.33 |
| Hypoxanthine | 0.0001-0.0011 | 2.19 | 0.55 | 0.33 |

*Total Plasma Volume = 2.28 Liters
**Refer to 2000 Report by Dr. Lobe

The treatment of stored LR-RBCs with Rejuvesol®, either concurrently or post storage prior to transfusion resulting in greater restoration of 2,3-DPG. Even though the pre-treatment packed cell weight of the LR-RBC units were greater than the NLR-RBC units (Table 1), recent studies demonstrate that the invention resulted in significantly higher concentration of 2,3-DPG to levels in LR-RBC derived from 500 mL of whole blood (WB) that were treated Rejuvesol® solution when compared to NLR-RBC that were derived from 450 mL of WB (Table 2).

TABLE 2

Pre-rejuvenation Net RBC Weight (grams)

| LR-RBC Derived from | NLR-RBC Derived from 450 mL | |
|---|---|---|
| 350.1 | 338.1 | Mean (n = 14} |
| 18.3 | 19.5 | SD |
| 318.9-379.0 | 305.0-366.5 | Range |

TABLE 3

Summary; ATP and 2,3-DPG values after rejuvenation, deglycerolization, and 24-post deglycerolization

| LR-RBC Derived from 500 mL of WB | | NLR-RBC Derived from 450 mL of WB | | |
|---|---|---|---|---|
| ATP (µmol/gHbg} | 2,3-DPG (µmol/gHbg) | ATP (µmol/gHbg) | 2,3-DPG (µmol/gHbg) | |
| 7.94 | 11.04 | 7.55 | 8.13 | Mean Post-Rej (n = 14} |
| 1.09 | 1.54 | 0.73 | 1.60 | SD |
| 5.89-9.60 | 9.05-13.68 | 6.27-8.75 | 5.75-11.01 | Range |
| NS | † | NS | † | †p < 0.0001 |
| | | | | NS p < 0.27 |
| 7.50 | 16.72 | 7.82 | 13.91 | Mean Post Delyc (n = 13} |
| 0.48 | 1.64 | 0.68 | 1.89 | SD |
| 6.62-8.94 | 13.67-19.58 | 6.80-9.20 | 11.17-17.29 | Range |
| NS | * | NS | * | *P < 0.0005 (n = 13} |
| | | | | NS p < 0.77 |
| 7.59 | 17.73 | 8.39 | 15.64 | Mean 24-hr Post Deglyc (n = 14} |
| 0.85 | 2.08 | 0.91 | 1.48 | SD |
| 6.62-9.05 | 13.42-20.87 | 6.76-9.53 | 12.73-18.59 | Range |
| NS | + | NS | + | +p < 0.0058 |
| | | | | NS p < 0.77 |

The embodiments and the examples described herein are exemplary and not intended to be limiting in describing the full scope of compositions and methods of the present technology. Equivalent changes, modifications and variations of embodiments, materials, compositions and methods can be made within the scope of the present technology, with substantially similar results.

Non-Limiting Discussion of Terminology

The headings (such as "Introduction" and "Summary") and sub-headings used herein are intended only for general organization of topics within the present disclosure, and are not intended to limit the disclosure of the technology or any aspect thereof. In particular, subject matter disclosed in the "Introduction" may include novel technology and may not constitute a recitation of prior art. Subject matter disclosed in the "Summary" is not an exhaustive or complete disclosure of the entire scope of the technology or any embodiments thereof. Classification or discussion of a material within a section of this specification as having a particular utility is made for convenience, and no inference should be drawn that the material must necessarily or solely function in accordance with its classification herein when it is used in any given composition or method.

The description and specific examples, while indicating embodiments of the technology, are intended for purposes of illustration only and are not intended to limit the scope of the technology. Moreover, recitation of multiple embodiments having stated features is not intended to exclude other embodiments having additional features, or other embodiments incorporating different combinations of the stated features. Specific examples are provided for illustrative purposes of how to make and use the compositions and methods of this technology and, unless explicitly stated otherwise, are not intended to be a representation that given embodiments of this technology have, or have not, been made or tested. Equivalent changes, modifications and variations of some embodiments, materials, compositions and methods can be made within the scope of the present technology, with substantially similar results.

As used herein, the words "preferred" or "preferable" refer to embodiments of the technology that afford certain benefits, under certain circumstances. However, other embodiments may also be desirable, under the same or other circumstances. Furthermore, the recitation of one or more desired embodiments does not imply that other embodiments are not useful, and is not intended to exclude other embodiments from the scope of the technology.

Although the open-ended term "comprising," as a synonym of non-restrictive terms such as including, containing, or having, is used herein to describe and claim embodiments of the present technology, embodiments may alternatively be described using more limiting terms such as "consisting of" or "consisting essentially of." Thus, for any given embodiment reciting materials, components or process steps, the present technology also specifically includes embodiments consisting of, or consisting essentially of, such materials, components or processes excluding additional materials, components or processes (for consisting of) and excluding additional materials, components or processes affecting the significant properties of the embodiment (for consisting essentially of), even though such additional materials, components or processes are not explicitly recited in this application. For example, recitation of a composition or process reciting elements A, B and C specifically envisions embodiments consisting of, and consisting essentially of, A, B and C, excluding an element D that may be recited in the art, even though element D is not explicitly described as being excluded herein.

As used herein, the word "include," and its variants, is intended to be non-limiting, such that recitation of items in a list is not to the exclusion of other like items that may also be useful in the materials, compositions, devices, and methods of this technology. Similarly, the terms "can" and "may" and their variants are intended to be non-limiting, such that recitation that an embodiment can or may comprise certain elements or features does not exclude other embodiments of the present technology that do not contain those elements or features.

Disclosure of values and ranges of values for specific parameters (such as temperatures, molecular weights, weight percentages, etc.) are not exclusive of other values and ranges of values useful herein. It is envisioned that two or more specific exemplified values for a given parameter may define endpoints for a range of values that may be claimed for the parameter. For example, if Parameter X is exemplified herein to have value A and also exemplified to have value Z, it is envisioned that parameter X may have a range of values from about A to about Z. Similarly, it is envisioned that disclosure of two or more ranges of values for a parameter (whether such ranges are nested, overlapping or distinct) subsume all possible combination of ranges for the value that might be claimed using endpoints of the disclosed ranges. For example, if parameter X is exemplified herein to have values in the range of 1-10, or 2-9, or 3-8, it is also envisioned that Parameter X may have other ranges of values including 1-9, 1-8, 1-3, 1-2, 2-10, 2-8, 2-3, 3-10, and 3-9.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

What is claimed is:

1. A method for treating or preventing ischemia in a human or other mammalian subject, comprising:
   (a) obtaining a volume of fresh blood from the subject;
   (b) performing a separation on the fresh blood, wherein plasma and leukocytes are delivered to the subject, and fresh red blood cells are isolated;
   (c) rejuvenating the fresh red blood cells with an enhancement composition to form rejuvenated fresh red blood cells, wherein the rejuvenated fresh red blood cells have adenosine triphosphate (ATP) and 2,3-diphosphoglycerate (2,3-DPG) levels equal to or greater than ATP and 2,3-DPG levels normally found in the subject's blood; and
   (d) delivering the rejuvenated fresh red blood cells to the subject, wherein the performing a separation, rejuvenating and delivering are performed within about 24 hours of the time of obtaining the fresh blood from the subject.

2. The method according to claim 1, wherein the enhancement composition comprises:
   (i) from about 25 g/L to about 30 g/L of inosine;
   (ii) from about 0.2 g/L to about 2 g/L of adenine;
   (iii) from about 5 g/L to about 15 g/L of pyruvate; and
   (iv) from about 17 g/L to about 23 g/L of sodium phosphate.

3. The method according to claim 1, further comprising performing a diagnostic test on the rejuvenated red blood cells.

4. The method according to claim 3, wherein the diagnostic test measures the concentrations of 2,3-diphosphoglycerate (2,3-DPG) or adenine triphosphate (ATP) in the rejuvenated red blood cells.

5. The method according to claim 4, further comprising calculating the volume of rejuvenated blood necessary to dose the subject to obtain normal or higher levels of 2,3-DPG and/or ATP in the subject.

6. The method according to claim 3, wherein the diagnostic test is performed by a device physically attached to the unit of blood.

7. The method according to claim 3, wherein the diagnostic test comprises collecting a sample of blood on a tag, a chip, a glass plate, or a pregnancy test-style strip.

8. The method according to claim 1, wherein the method is performed in anticipation of surgery on the subject.

9. The method according to claim 1, wherein rejuvenating the red blood cells results in red blood cell 2,3-diphosphoglycerate (2,3-DPG) concentration of greater than about 15 μmol/L/gHb.

10. A method of enhancing the ability of blood to oxygenate tissue in a subject in need thereof comprising:
    (a) obtaining a unit of fresh blood;
    (b) performing a first diagnostic test on the fresh blood to determine the concentration of a marker selected from 2,3-diphosphoglycerate (2,3-DPG), adenine triphosphate (ATP), or combinations thereof;
    (c) contacting the fresh blood with an enhancement composition to form rejuvenated fresh blood;
    (d) performing a second diagnostic test on the rejuvenated fresh blood to determine the concentration of the marker;
    (e) comparing the concentration of the marker from the first diagnostic test to the concentration of the marker from the second diagnostic test and determining a volume of rejuvenated fresh blood necessary to dose the subject to normal or higher levels of 2,3-DPG and/or ATP in the subject's systemic circulation; and
    (f) administering the volume of rejuvenated fresh blood, determined in step (e) to the subject;
    wherein the obtaining, performing a first diagnostic test, contacting, performing a second diagnostic test, comparing and administering are performed within about 24 hours of the time of obtaining the fresh blood from the subject.

11. The method according to claim 10, wherein the unit of blood is autologous to the subject.

12. The method according to claim 10, wherein the enhancement composition comprises:
  (i) from about 25 g/L to about 30 g/L of inosine;
  (ii) from about 0.2 g/L to about 2 g/L of adenine;
  (iii) from about 5 g/L to about 15 g/L of pyruvate; and
  (iv) from about 17 g/L to about 23 g/L of sodium phosphate.

13. The method according to claim 12, wherein the diagnostic test is performed on a chip.

14. The method according to claim 12, wherein the subject is in anticipation of surgery.

15. A method of performing a transfusion comprising:
  (a) obtaining a unit of fresh blood;
  (b) performing a diagnostic test on the unit of fresh blood to determine 2,3-diphosphoglycerate (2,3-DPG) concentration in the blood;
  (c) rejuvenating the fresh blood if the 2,3-DPG concentration is lower than about 10 µmol/L/gHb to form rejuvenated fresh blood, wherein the rejuvenating is performed with an enhancement composition comprising, inosine, adenine, pyruvate, and sodium phosphate; and
  (d) delivering the rejuvenated fresh blood to a subject in need thereof;
wherein the obtaining, performing a diagnostic test, rejuvenating and delivering are performed within about 24 hours of the time of obtaining the fresh blood from the subject.

16. A method for treating or preventing ischemia in a human or other mammalian subject, comprising:
  (a) obtaining a volume of fresh blood from the subject;
  (b) performing a separation on the fresh blood, wherein plasma and leukocytes are delivered to the subject, and fresh red blood cells are isolated;
  (c) rejuvenating the fresh red blood cells with an enhancement composition to form rejuvenated fresh red blood cells, wherein the concentration of 2,3-diphosphoglycerate (2,3-DPG) concentration in the rejuvenated red blood cells is greater than about 15 µmol/L/gHb; and
  (d) delivering the rejuvenated fresh red blood cells to the subject;
wherein the obtaining, performing a separation, rejuvenating, and administering are performed within about 24 hours of the time of obtaining the fresh blood from the subject.

17. The method according to claim 16, wherein the delivering of the rejuvenated fresh red blood cells is performed within 6 hours after the obtaining of the volume of fresh blood from the subject.

18. The method according to claim 16, wherein the enhancement composition comprises:
  (i) from about 25 g/L to about 30 g/L of inosine;
  (ii) from about 0.2 g/L to about 2 g/L of adenine;
  (iii) from about 5 g/L to about 15 g/L of pyruvate; and
  (iv) from about 17 g/L to about 23 g/L of sodium phosphate.

19. The method according to claim 16, further comprising performing a diagnostic test on the rejuvenated fresh red blood cells, measuring the concentrations of 2,3-diphosphoglycerate (2,3-DPG) or adenine triphosphate (ATP) in the rejuvenated red blood cells.

20. The method according to claim 16, wherein the method is performed in anticipation of surgery on the subject.

* * * * *

UNITED STATES PATENT AND TRADEMARK OFFICE
CERTIFICATE OF CORRECTION

| | | |
|---|---|---|
| PATENT NO. | : 9,103,842 B2 | Page 1 of 1 |
| APPLICATION NO. | : 13/844773 | |
| DATED | : August 11, 2015 | |
| INVENTOR(S) | : Gray et al. | |

It is certified that error appears in the above-identified patent and that said Letters Patent is hereby corrected as shown below:

In the claims

In column 20, line 59, in Claim 10, delete "blood," and insert --blood--, therefor Signed and Sealed this
Fifteenth Day of December, 2015

Michelle K. Lee
*Director of the United States Patent and Trademark Office*